US006627416B1

(12) United States Patent
Faulstich et al.

(10) Patent No.: US 6,627,416 B1
(45) Date of Patent: Sep. 30, 2003

(54) 5'-MODIFIED NUCLEOTIDES AND THE APPLICATION THEREOF IN MOLECULAR BIOLOGY AND MEDICINE

(75) Inventors: Konrad Faulstich, Heidelberg (DE); Wilhelm Ansorge, Heidelberg (DE)

(73) Assignee: Europaisches Laboratorium fur Molekularbiologie (EMBL) (DE)

(*) Notice: Subject to any disclaimer, the term of this patent is extended or adjusted under 35 U.S.C. 154(b) by 0 days.

(21) Appl. No.: 09/646,890

(22) PCT Filed: Apr. 6, 1999

(86) PCT No.: PCT/EP99/02320

§ 371 (c)(1),
(2), (4) Date: Jan. 10, 2001

(87) PCT Pub. No.: WO99/53087

PCT Pub. Date: Oct. 21, 1999

(30) Foreign Application Priority Data

Apr. 8, 1998 (DE) .......................................... 198 15 864

(51) Int. Cl.[7] .......................... C12Q 1/68; C12P 19/34; C07H 21/00; C07H 21/02
(52) U.S. Cl. ........................ 435/91.1; 435/6; 435/91.2; 435/128; 435/130; 536/22.1; 536/23.1; 536/25.3
(58) Field of Search .......................... 435/6, 91.1, 91.2, 435/128, 130; 536/22.1, 23.1, 25.3

(56) References Cited

FOREIGN PATENT DOCUMENTS

| DE | 34 46 635 | 6/1985 |
| WO | 95 06752 | 3/1995 |
| WO | 96 19572 | 6/1996 |

OTHER PUBLICATIONS

Letsinger et al. Biochemistry vol. 15, No. 13, 1976, pp. 2810–2816.*
Rooij et al. Tetrahedron vol. 35, 1979, pp. 2913–2926.*
Matthews et al. Analytical Biochemistry vol. 169, 1988, pp. 1–25.*
Letsinger, Robert et al "Nucleotide chemistry. XVII. Enzymic synthesis of polydeoxyribonucleotides processing . . . ", J. Amer. Chem. Soc., vol. 94, No. 1, 1972, pp. 292–293.
Chen et al., "5–Iodo–5'–amino–2', 5'–dideoxyuridine–5'–N'–triphosphate. Synthesis, chemical properties . . . ", J. Biol. Chem, vol. 251, No. 16, 1976, pp. 4839–4841.
Mag et al., "Synthesis and selective cleavage of oligodeoxyribonucleotides containing non–chiral . . . ", Nucleic Acids Res., vol. 17, No. 15, 1989, pp. 5973–5988.
Mag et al., "Synthesis and selective cleavage of an oligodeoxynucleotide containing a bridged internucleotide . . . ", Nucleic Acids Res., vol. 19, No. 7, 1991, pp. 1437–1441.
Trowbridge et al., "Ring openings of trimetaphosphroic acid and its bismethylene analog . . . ", J. Amer. Chem. Soc., vol. 94, No. 11, 1972, pp. 3816–3824.
Patel et al., "5'–Deoxy–5'–thioribonucleoside–5'–triposphates", Tetrahedron Lett., vol. 38, No. 6, 1997, pp. 1021–1024.

* cited by examiner

*Primary Examiner*—Jezia Riley
(74) *Attorney, Agent, or Firm*—Rothwell, Figg, Ernst & Manbeck

(57) ABSTRACT

The invention relates to 5'-modified nucleotides and to nucleic acids which contain these nucleotides. Processes for incorporating the 5'-modified nucleotides into nucleic acids, and the subsequent site-specific cleavage of the nucleic acids at the 5'-modified monomer building blocks, are also disclosed. These processes can be employed for nucleic acid sequencing, for generating nucleic acid libraries, for detecting mutations, for preparing support-bound nucleic acids and for pharmaceutical purposes.

21 Claims, 13 Drawing Sheets

FIG.1
A
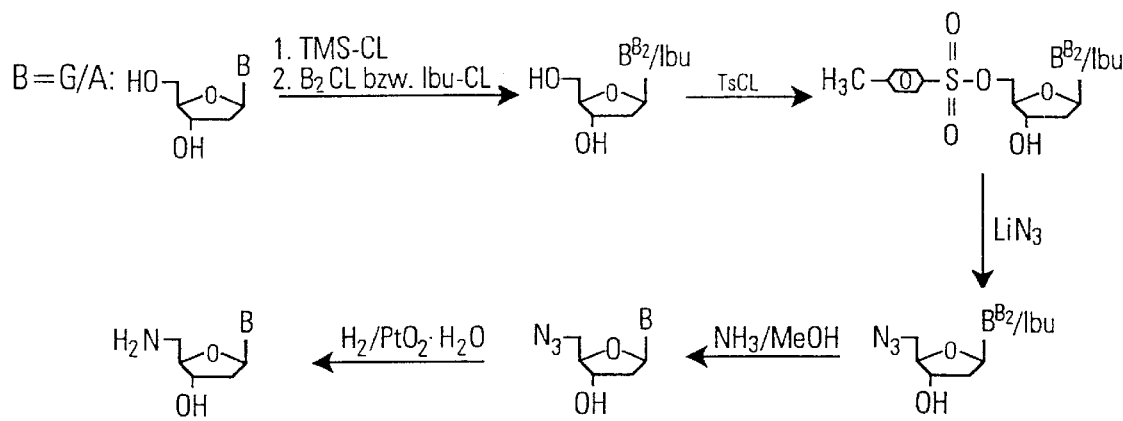
B
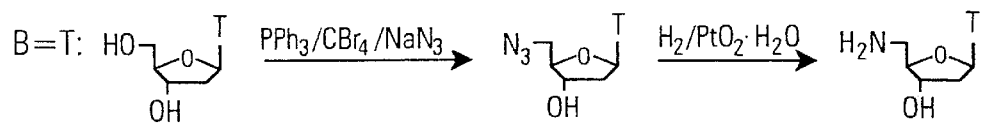
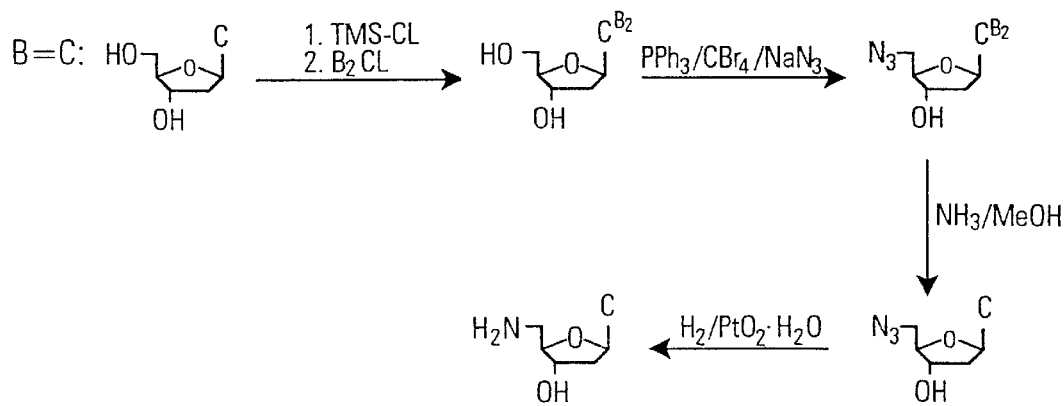

B = A, C, G, T

5'-MODIFIED NUCLEOTIDES AND THE APPLICATION THEREOF IN MOLECULAR BIOLOGY AND MEDICINE

This application claims priority to PCT International Application No. EP99/02320 filed on Apr. 6, 1999, which claims priority to German Application No. 19815864.5 filed on Apr. 8, 1998.

The invention relates to 5'-modified nucleotides and to nucleic acids which contain these nucleotides. Processes for incorporating the 5'-modified nucleotides into nucleic acids, and the subsequent site-specific cleavage of the nucleic acids at the 5'-modified monomer building blocks, are also disclosed. These processes can be employed for nucleic acid sequencing, for generating nucleic acid libraries, for detecting mutations, for preparing support-bound nucleic acids and for pharmaceutical purposes.

The processes which are nowadays routinely used for sequencing nucleic acids generally comprise polymerizing a nucleic acid strand which is complementary to a template and generating a mixture of nucleic acid fragments of all possible lengths (1). This nucleic acid fragment mixture can be obtained by terminating the polymerization or degrading using exonucleases (2), by iterative sequencing methods (3), by adding individual bases and detecting the release of pyrophosphate (4), by chemical methods using elimination reactions (5), by chemicoenzymic methods, involving incorporating modified nucleosides and cleaving by attack on phosphorothioate- or boron-modified nucleotides (6), by incorporating ribonucleosides into DNA and subsequently cleaving under basic conditions (7) or by incorporating 3'-dye-labelled nucleotides while at the same time or subsequently eliminating the dye (8). In addition to these methods, strategies are also available which involve sequencing by hybridizing (9) and a physical production of fragments by means of mass spectrometry (10). The possibility of detecting by means of atomic force microscopy (11) has also been discussed.

However, in the last twenty years, the method of choice has been the enzymic chain termination method. This method makes possible automation and sequencing with high throughput for use when sequencing entire genomes. The automation was achieved by using dye primers (12), internal labelling (13) or dye terminators (14). Sequencing with dye primers and internal labelling suffer, however, from the disadvantage that irregular termination events occur in the sequence ladder and can lead to erroneous interpretation of the sequence data. Dye terminators suffer from the disadvantage that they are sometimes incorporated at incorrect sites and only permit a limited length to be read since they are modified substrates.

In this addition to this, there is a need to reduce the quantity of DNA which is required for a sequence determination. There is currently only one single cyclic sequencing method available for this purpose (15), which method, however, in contrast to PCR, in which an exponential amplification takes place, only leads to linear amplification of the products. The direct sequencing of PCR products in turn displays disadvantages since relatively large quantities of triphosphates and primer molecules are present in the reaction vessels and can lead to impairment of the sequencing reaction or the sequence determination (16). However, the purification of the PCR products is time-consuming and represents an additional procedural step. While triphosphates can be cleaved using enzymic methods (17), this is also time-consuming and increases the costs of carrying out the sequencing reaction. As an alternative, a direct exponential amplification and sequencing method (DEXAS) is available for sequencing small quantities of DNA material (18); however, it has so far not been possible to use this method for a standard sequencing and, in contrast to its name, the method is not directly exponential.

The present invention makes available a novel process for sequencing nucleic acid, which process at least partially avoids the disadvantages of the state of the art. In particular, this process avoids the problem of substrate specificity with regard to dye terminators and makes possible rapid DNA sequencing using very small quantities of DNA starting material in combination with a nucleic acid amplification reaction such as PCR. The process also improves the readable length of the sequenceable templates.

The process according to the invention is based on using compounds of the general formula (I):

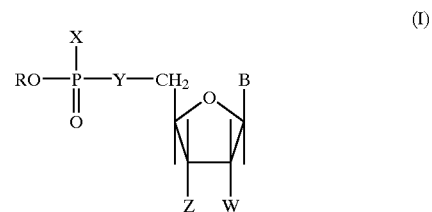

in which:

B denotes a nucleobase, i.e. a natural or unnatural base which is suitable for hybridizing to complementary nucleic acid strands, such as A, C, G, T, U, I, 7-deaza-G, 7-deaza-A, 5-methyl-C, etc., W and Z in each case denote $OR^1$, $SR^1$, $N(R^1)_2$ or $R^1$, where $R^1$, in each case independently, on each occurrence represents hydrogen or an organic radical, e.g. an alkyl, alkenyl, hydroxyalkyl, amine, ester, acetal or thioester radical, preferably having up to 10 carbon atoms and particularly preferably having up to 6 carbon atoms, X denotes $OR^2$, $SR^2$ or $B(R^2)_3$, where $R^2$, in each case independently, denotes hydrogen, a cation, e.g. an alkali metal ion or ammonium ion, or an organic radical, e.g. a dye such as fluorescein, rhodamine, cyanine and their derivatives, Y denotes $NR^3$ or S, in particular $NR^3$, where $R^3$ represents hydrogen or an organic radical, e.g. a saturated or unsaturated hydrocarbon radical, in particular a $C_1$–$C_4$ radical or a dye radical, with hydrogen also being understood to mean the isotopes deuterium and tritium, and R denotes hydrogen, a cation, an organic radical or an optionally modified phosphate group or diphosphate group, in particular a diphosphate group, for incorporation into nucleic acids and for the subsequent site-specific cleavage of the nucleic acids, preferably by hydrolysing the P—Y bond, resulting in the formation of nucleic acid fragments having an HY—$CH_2$-5' end.

The group R can denote an organic radical, for example a lipophilic radical, which facilitates the penetration of the substance into a cell. R is preferably a phosphate group:

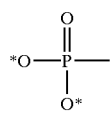

or a diphosphate group:

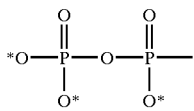

This phosphate or diphosphate group can be modified. Thus, one or more terminal oxygen atoms can carry substituents, e.g. organic radicals. On the other hand, one or more terminal oxygen atoms and, in the case of the diphosphate group, the bridging oxygen atom as well, can be replaced by groups such as S, $NR^3$ or $C(R^3)_2$, with $R^3$ being defined as before. In addition to this, 2 substituents on terminal oxygen atoms can also be bridged with each other.

When substituents are present, they are preferably located on oxygen atoms belonging to the phosphorus atom which is in each case terminal, particularly preferably on the γ-phosphorus atom. Examples of suitable substituents are organic radicals such as alkyl radicals, which can themselves be substituted, or a salicyl group, which can form a 6-membered cyclic diester with 2 oxygen atoms belonging to the terminal phosphorus. The aromatic nucleus of the salicyl groups can again itself carry one or more additional substituents, e.g. those defined as for $R^1$ or halogen atoms. Additionally preferred substituents on the oxygen atom are radicals such as $C_1$–$C_{10}$-alkyl, —$(CH_2)_n$—$N_3$, $(CH_2)_n N(R^3)_2$ or —$(CH_2)_n NHOCO(CH_2)_m$—$N(R^3)_2$, where n and m are integers from 1 to 8, preferably from 2 to 5, and $R^3$ is defined as above, but can, in addition, preferably denote an aromatic radical such as phenyl or dinitrophenyl.

The incorporation of compounds of the general formula (I) into nucleic acids preferably takes place enzymically. However, a chemical synthesis is also possible. For an enzymic incorporation, preference is given to using enzymes which are selected from the group consisting of DNA-dependent DNA polymerases, DNA-dependent RNA polymerases, RNA-dependent DNA polymerases, RNA-dependent RNA polymerases and terminal transferases. Particular preference is given to T7 DNA polymerase and related enzymes, such as T3 DNA polymerase or SP6 DNA polymerase, or modifications of these enzymes. Correspondingly, the nucleic acids into which the compounds of the formula (I) are incorporated can be DNAs and/or RNAs which can, where appropriate, carry one or more additional modified nucleotide building blocks.

Nucleic acids which contain, as monomeric building blocks, at least one compound of the general formula (I) can be cleaved site-specifically at the nucleotide building block which contains the P—Y bond. This site-specific cleavage can be effected, for example, at the P—Y bond itself by raising the temperature, e.g. to at least 37° C., by instigating acid conditions, e.g. pH≦5, by microwave treatment or by laser treatment, e.g. using an infrared laser, and/or on the 3' side of the nucleotide containing the P—Y bond by means of enzymic digestion, for example using exonucleases or endonucleases or phosphodiesterases, e.g. 3'→15' snake venom phosphodiesterase.

The process according to the invention can also be carried out in combination with an amplification reaction, e.g. a PCR. This enables extremely small quantities of DNA starting material to be used for generating labelled complementary nucleic acid strands. The nucleic acid amplification is preferably carried out using thermostable enzymes in several cycles.

The compounds according to (I) can be incorporated into the nucleic acids in solution. Alternatively, however, the compounds can also be incorporated into support-bound nucleic acids. After the synthesis, the nucleic acids can then be released from the support, where appropriate by site-specific cleavage of the P—Y bond, or by other methods.

The site-specific cleavage of the nucleic acids results in the production of nucleic acid fragments which preferably possess the group Y—$CH_2$— at their 5' ends and/or a phosphate group at their 3' ends. Previously, nucleic acids which had been modified in this way had to be produced in a complicated manner by means of chemical synthesis (19) or by means of enzymic reactions (20, 21). The process according to the invention is considerably faster and cheaper and enables the compounds to be handled more easily. The modified nucleic acids which are prepared in this way can be used for therapeutic purposes and/or for molecular biological investigations, e.g. investigations of mechanisms for the uptake and metabolism of nucleic acids in cells, since it is readily possible to couple a labelling group to the 5'-Y group. The 3' phosphate group in turn constitutes a protecting group in relation to a ligation and/or an enzymic elongation using polymerases. If desired, labelling groups can be added to the phosphorylated 3' end of the nucleic acid fragments, e.g. if a dephosphorylation is carried out and oligonucleotides, which are labelled by an enzymic reaction, for example using ligase or terminal transferase, or dideoxynucleoside triphosphates, which are labelled using a polymerase, are added to the resulting 3'-OH group, or if the 3'-phosphate group contains a reactive group, e.g. a sulphur atom.

Furthermore, as a consequence of the defined group at their 5' ends, the nucleic acid fragments according to the invention can readily be immobilized on a support which contains a functional surface which reacts with the Y group. On the other hand, it is also possible for the nucleic acid fragments to bind adsorptively to a surface by way of the Y group. Suitable supports are those which possess surfaces which are composed, for example, of metal, glass, ceramic and/or plastic. Particular preference is given to supports which possess glass and/or silicon surfaces. The supports can furthermore be of any desired form, e.g. microparticles, such as magnetic microparticles, or semiconductor materials, such as biochips, e.g. DNA or RNA chips, which, where appropriate, can contain several defined surfaces, in the form of array arrangements, which are able to bind specifically to nucleic acids.

The nucleic acid fragments according to the invention can also be coupled to a support when they are in the form of a mixture of different fragments. This results in the production of supports on which nucleic acid fragments are arranged randomly. This has advantages if, for example, a subsequent amplification is carried out on the support surface using primers which encode a predetermined nucleic acid sequence, for example a gene.

If a heterogeneous nucleic acid mixture is produced when the nucleic acids are cleaved, this mixture can then be used for preparing a nucleic acid library, in particular a random library. Such libraries can also be produced by means of multiple, random incorporation of compounds of the formula (I) into a nucleic acid strand followed by site-specific cleavage. In addition, degenerate primers, which bind randomly to nucleic acid templates, can also be employed for generating random nucleic acid libraries.

The fragments in the nucleic acid library can be reassembled combinatorially either without or after further enzymic or chemical treatment (DNA shuffling). Since the 5' end of each fragment is provided with a Y group (with the exception of the 5' end of the first fragment), the other fragments can only be assembled such that the. original first fragment forms the first fragment once again. The complete combinatorial scope can be exploited after having subjected the library, or individual fragments from it, to further enzymic or chemical treatment.

After the site-specific cleavage, the nucleic acid fragments which have been produced by the process according to the invention can be subjected to a detection reaction. This detection reaction can be effected using any methods which are known for this purpose. Preference is given to carrying out a mass spectrometric analysis and/or an electrophoresis, e.g. a polyacrylamide gel electrophoresis.

The detection reaction can, for example, be employed for detecting mutations, e.g. point mutations in nucleic acids. Two protocols for analysing point mutations are described in detail below.

Another important application of the process according to the invention is that of nucleic acid sequencing. Such sequencing processes can be carried out in a number of different variants. For example, the process according to the invention is also suitable for carrying out a cyclic sequencing in combination with a nucleic acid amplification and/or a bidirectional sequence analysis on one nucleic acid strand. Preferred examples of sequencing processes are described in detail below.

The present invention also relates to a pharmaceutical composition which comprises, as the active component, a compound of the general formula (I), where appropriate in combination with pharmaceutically tolerated excipients, adjuvants and/or fillers. In addition to this, the invention also relates to pharmaceutical compositions which comprise, as the active component, a nucleic acid into which at least one compound of the general formula (I) has been incorporated, and also, where appropriate, pharmaceutically tolerated excipients, adjuvants and/or fillers. The pharmaceutical compositions are suitable for use as agents for gene therapy, as anti-viral agents and as anti-tumour agents, or for anti-sense applications.

Thus, nuclease-resistant 5'-amino compounds, or nucleic acids which contain these compounds, can be introduced into living cells and incorporated by cellular and/or viral enzymes, e.g. polymerases or reverse transcriptases, into nucleic acids in these cells. If the cellular polymerase is, for example, unable to read the modified genes, and does not even accept the modified triphosphates as substrates, the viral genetic information cannot then be amplified. Furthermore, the use of the 5'-modified 5'-nucleoside triphosphates results in the viral genes being disintegrated since the P—Y bond, in particular the P—N bond, which has been introduced is labile under physiological conditions.

The invention additionally relates to a process for preparing nucleic acid fragments, which process comprises the steps of:

(a) providing a nucleic acid which contains at least one compound of the general formula (I) as a monomeric building block, and (b) subjecting the nucleic acid to site-specific cleavage.

Compounds of the formula (I) according to the invention can be used as constituents of reagent kits for detecting nucleic acids, e.g. as sequencing kits or as kits for mutation analysis, where appropriate together with additional detection components. Examples of these additional detection components are enzymes, in particular polymerases, such as DNA polymerases or reverse transcriptases, oligonucleotides which can be used as primers and which can, where appropriate, carry a label at their 5' ends and/or on their side chains, deoxynucleoside triphosphates which can, where appropriate, carry a label, and dideoxynucleoside triphosphates (chain termination molecules) which can optionally carry a label, and also additional reagents, e.g. buffers, etc., and solid supports. The reagent kits according to the invention preferably comprise the constituents which are specified in the following figures.

The invention is additionally explained by the following figures and examples:

FIG. 1 shows a diagram of the synthesis of 5'-amino-modified nucleosides;

Processes for preparing compounds of the formula (I) according to the invention, in which Y represents an amino group, are shown in FIGS. 1a and b. FIG. 1a shows a scheme for preparing 5'-amino-2',5'-dideoxypurine nucleosides. For this, the amino groups of the nucleobase are blocked by reaction with protecting groups, e.g. by silylating with trimethylsilyl chloride and then introducing a Bz or Ibu protecting group. The 5'-OH group is then activated, e.g. by reaction with tosyl chloride, such that it is able to react with an alkali metal azide, e.g. $LiN_3$. After the protecting groups have been eliminated, e.g. using $NH_3$/MeOH, the protecting group can be converted reductively into an amino group, e.g. using $H_2/PtO_2$.

FIG. 1b shows a corresponding synthesis scheme for preparing 5'-amino-2',5'-dideoxypyrimidine nucleosides. Thymidine can, for example, be reacted directly with an azide salt, e.g. $NaN_3$, and the azide group can then be converted reductively into an amino group. In the case of cytidine, the nucleobase is first of all blocked with a protecting group, e.g. Bz, after which an azide group, which can be converted reductively into an amino group, can be introduced in a similar manner to that for thymidine.

Figure 2:
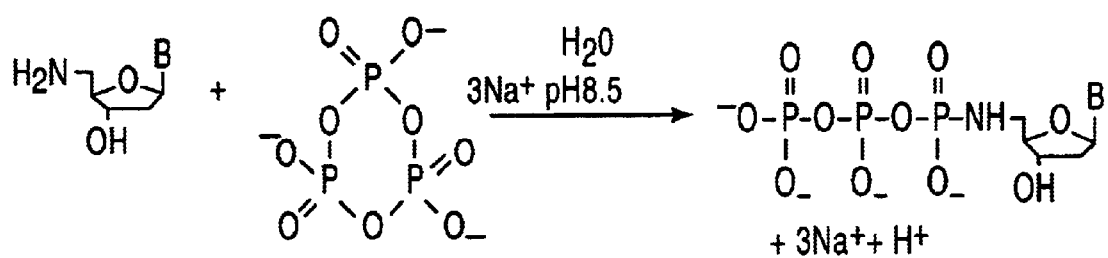
FIG. 2 shows a diagram of the preparation of 5'-amino-modified nucleoside triphosphates.

FIG. 2 shows a synthesis scheme for preparing 5'-amino-2',5'-dideoxynucleoside 5'-triphosphates which can be used to add, in a simple manner, a triphosphate group to the nucleosides which are obtained in accordance with FIG. 1. The 5'-aminonucleoside triphosphates which are prepared in this way can be used as monomeric building blocks for incorporation into nucleic acids. Detailed instructions for performing these reactions are given in Example 1.

Figure 3:
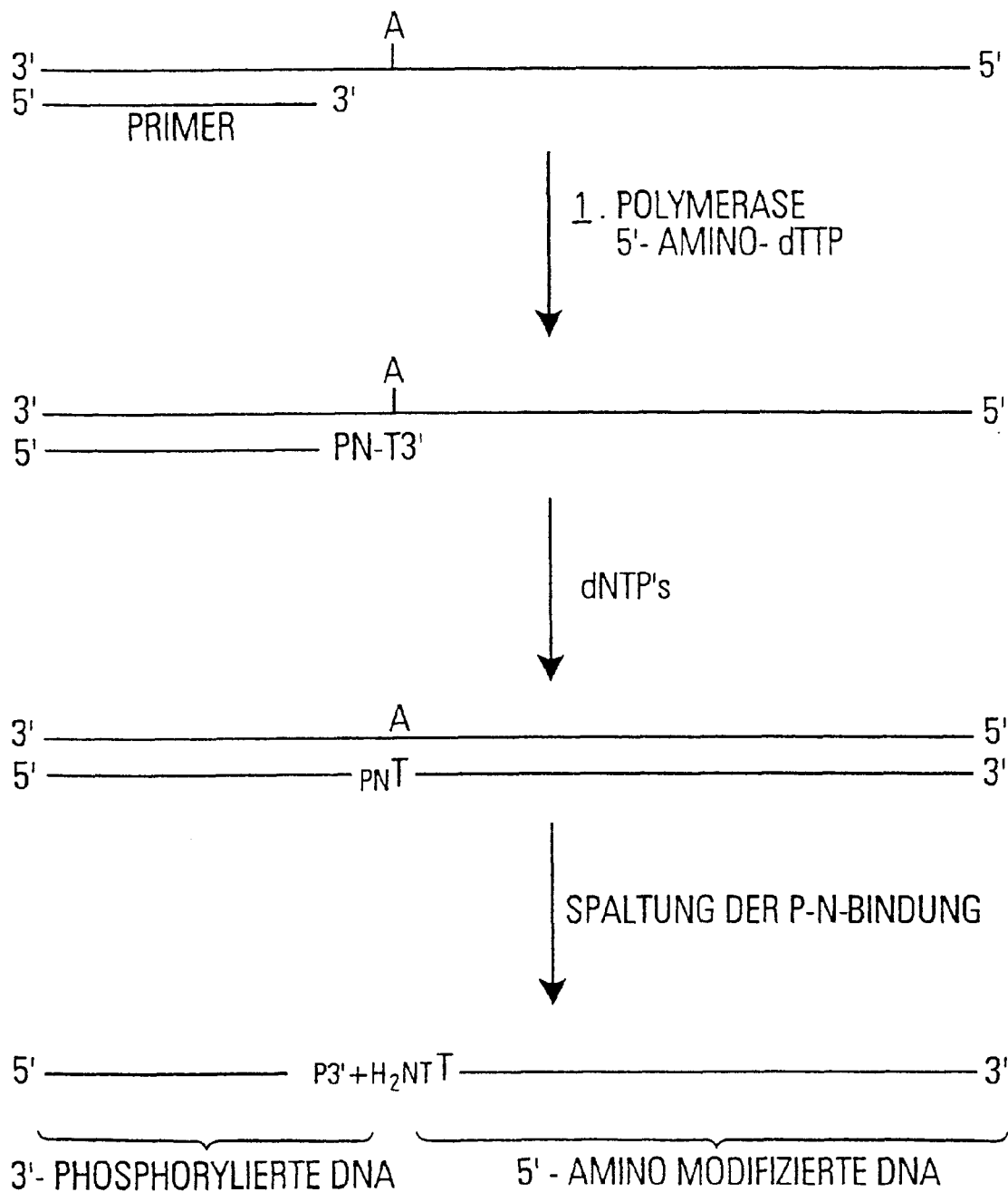
FIG. 3 shows a diagram of the generation of 5'-amino-modified and/or 3'-phosphorylated DNA fragments by the site-specific cleavage of the P—N bond in the case where 5'-amino nucleoside triphosphates have been incorporated.

FIG. 3 shows the generation of modified DNA fragments which contain a 5'-amino-T building block, and the subsequent cleavage of these DNA fragments at the P—N bond, with 3'-phosphorylated and/or 5'-amino-modified DNA fragments being obtained.

Figure 4:
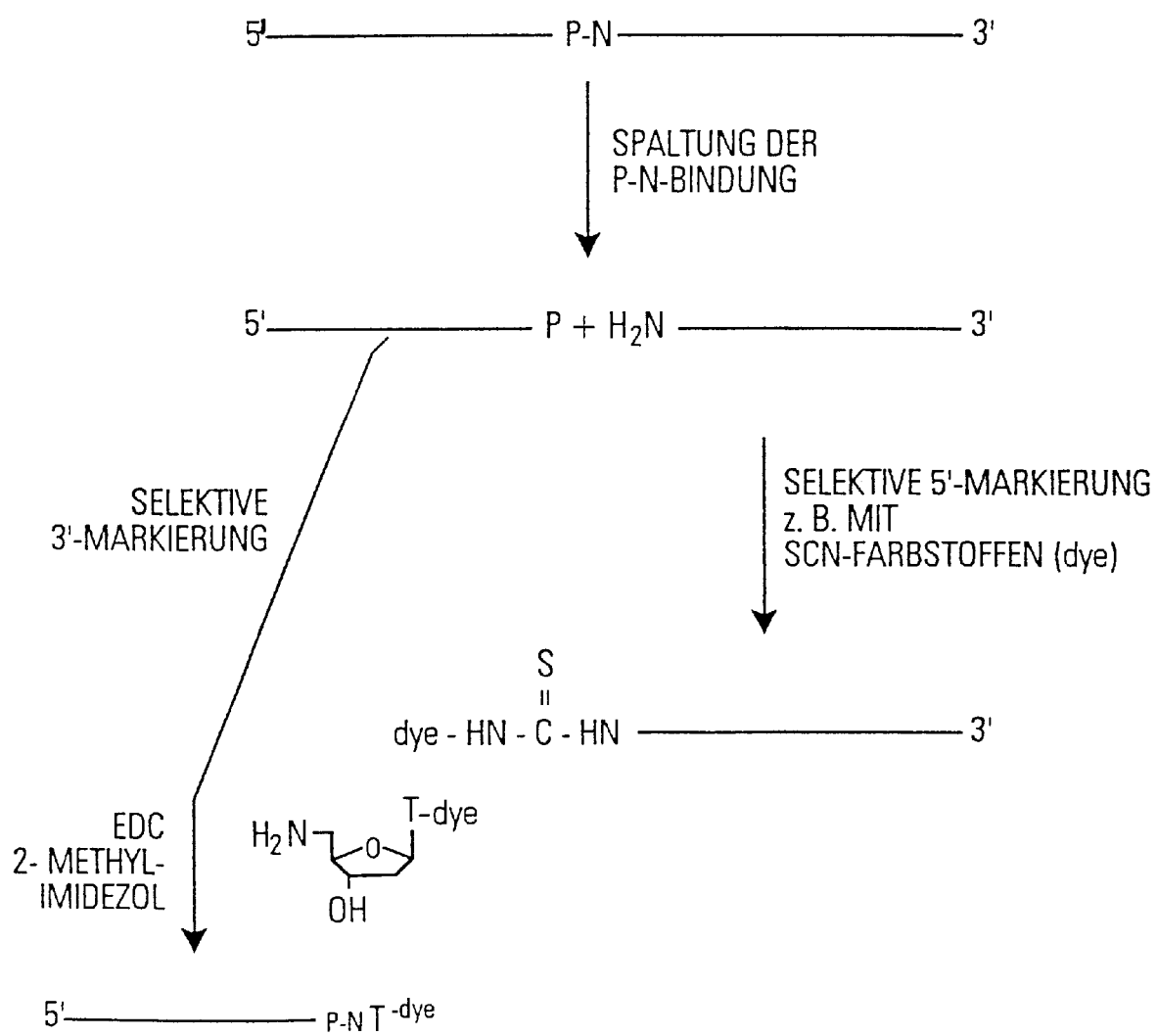
FIG. 4 shows a diagram of the selective 5'- or 3'-labelling of nucleic acid fragments.

FIG. 4 shows examples of selectively 5'- and 3'-labelling the nucleic acid fragments which the cleavage generates.

Figure 5:
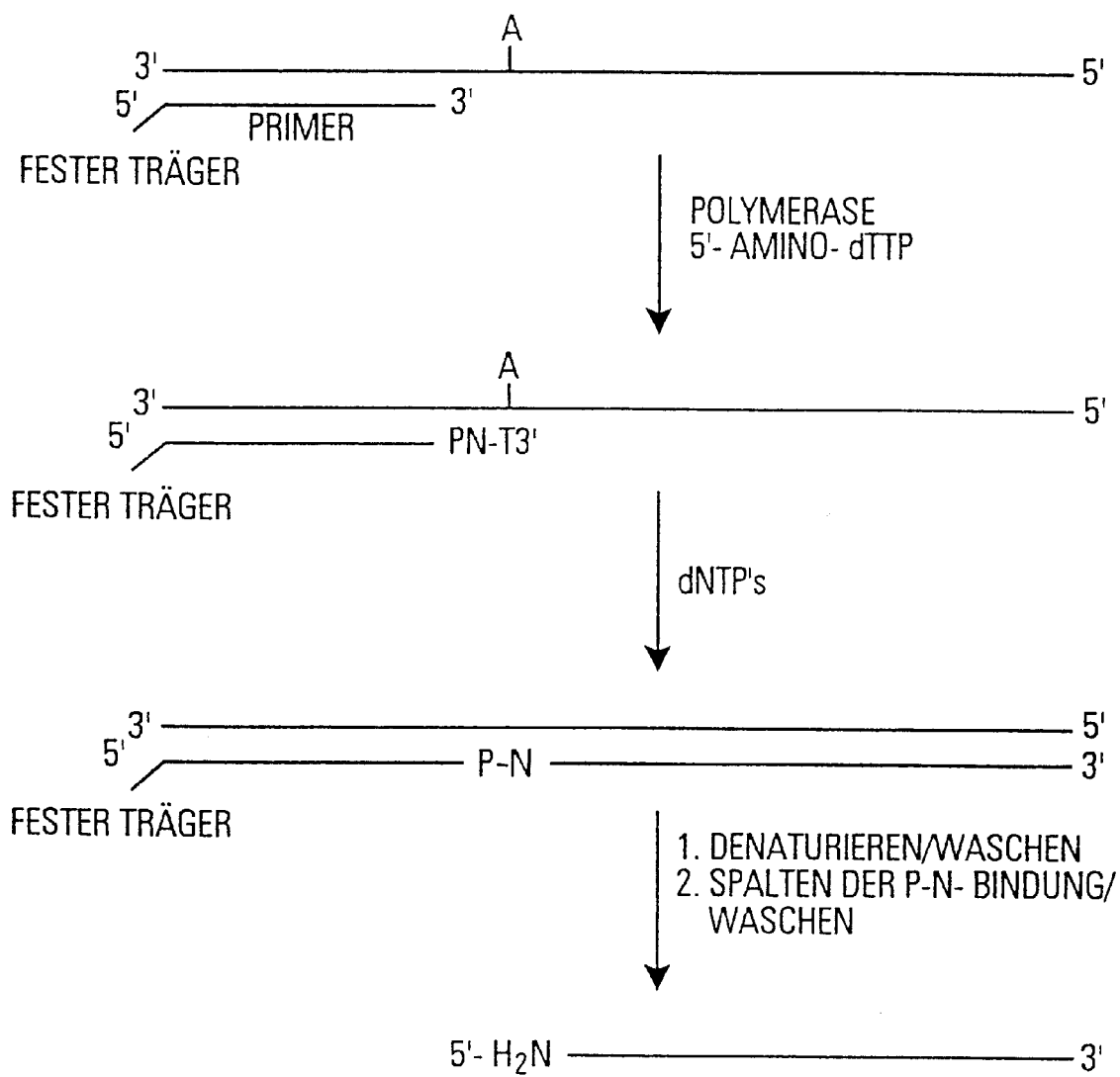
FIG. 5 shows a diagram of the elimination of nucleic acids from solid supports.

FIG. 5 shows the synthesis of 5'-aminonucleotide building block-containing DNA molecules on a solid support, and the subsequent liberation of 5'-amino-modified DNA fragments by cleavage of the P—N bond.

Figure 6:
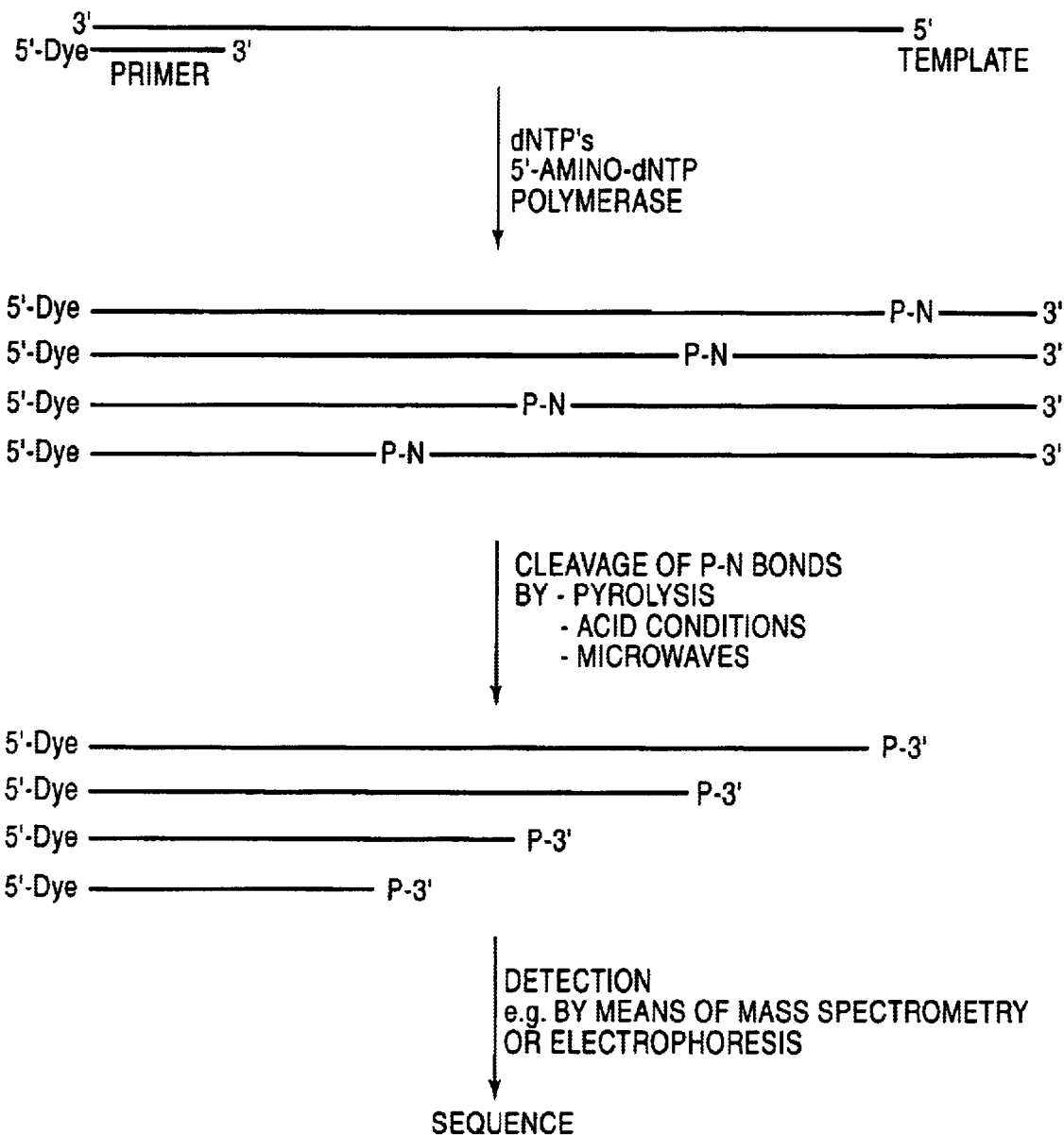
FIG. 6 shows a diagram of a sequencing protocol which uses a 5'-dye-labelled sequencing primer.

FIG. 6 shows a diagram of an embodiment of the 5'-amino sequencing process. The embodiment shown makes use of a primer which carries a labelling group at its 5' end and is extended by enzymic polymerization, with 5'-amino-modified nucleotides being incorporated into the nucleic acid strand at random positions. The modified nucleotides are accepted as substrates by DNA polymerases, e.g. by T7 DNA polymerase. The P—N bonds are distributed randomly over the nucleic acid strand and can be readily cleaved, for example by pyrolysis, acid conditions and/or microwave treatment, thereby giving rise to a mixture of nucleic acid fragments. Each of these fragments carries a phosphate group at its 3' end, thereby avoiding changes in mobility in a gel electrophoresis. When compounds of the formula (I) in which X denotes a detectable group, e.g. a dye group, are incorporated, nucleic acid fragments which have a label on their 3' nucleotide are obtained following cleavage.

The modified nucleotides can also be employed for a cyclic sequencing. When thermostable polymerases are used, it is possible firstly to amplify the DNA template, for example by PCR, and then to incorporate the modified nucleotides at 37° C. and using T7 DNA polymerase. The cleavage is then effected directly in the reaction vessel by simply heating at 95° C., for example. Alternatively, the modified nucleotides can already be incorporated during the amplification itself using a thermostable polymerase.

Following cleavage, the reaction mixture, or a part thereof, is subjected to a detection reaction, e.g. by means of gel electrophoresis. This avoids substrate specificity problems in the case of dye-labelled chain termination molecules. As compared with previously available chemicoenzymic methods, e.g. by incorporating α-thionucleotides, the process according to the invention enables the generated nucleic acid strands to be cleaved more readily without having to use aggressive chemicals which could attack the labelling group on the primer or the glycosidic bond. The process according to the invention can decrease the costs of existing sequencing protocols since the triphosphates can be prepared in a very simple manner, e.g. by the user himself, directly prior to sequencing. The process is rapid and simple and functions even with a very small quantity of DNA starting material.

Figure 7:
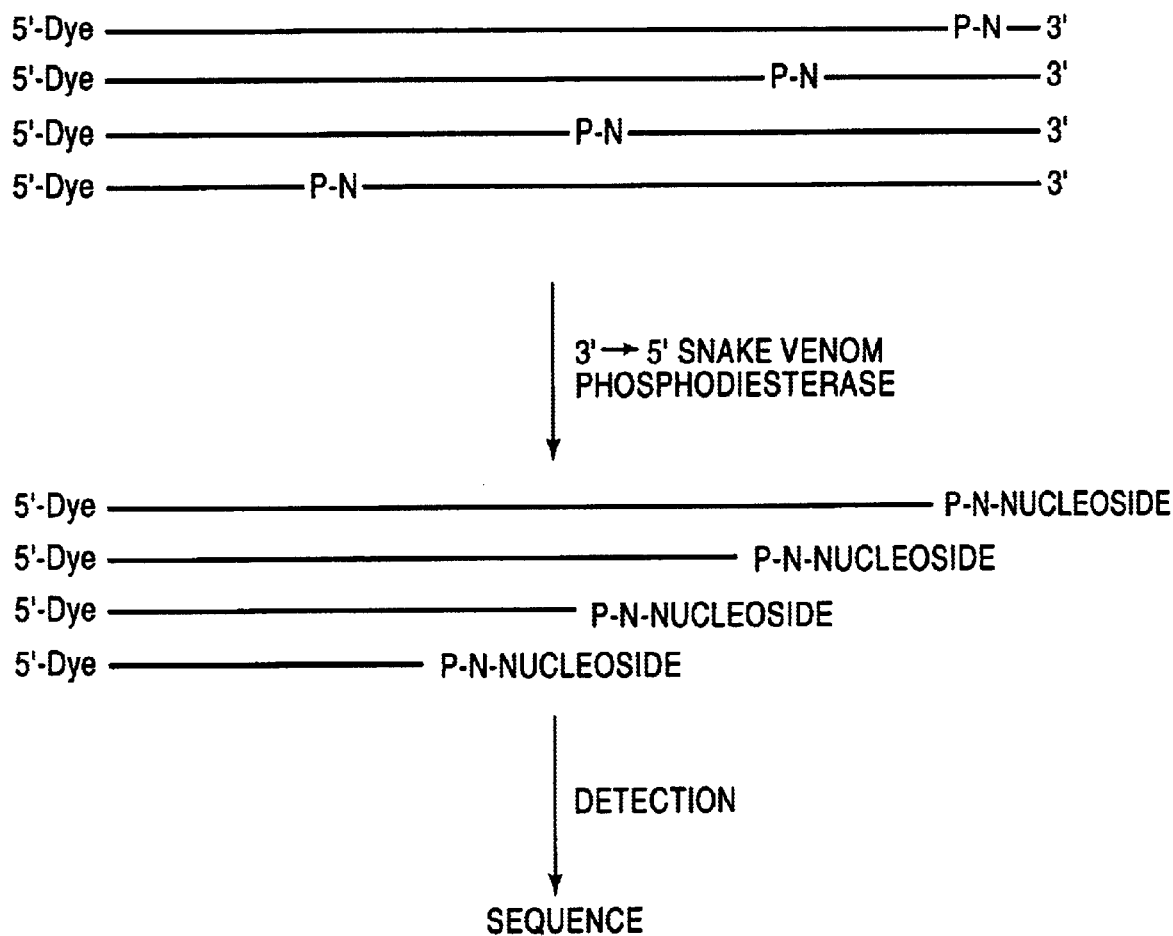
FIG. 7 shows an alternative process for generating sequenceable fragments by means of exonuclease digestion.

FIG. 7 shows an alternative method for generating sequenceable nucleic acid fragments by means of 3'→5'-exonuclease digestion, e.g. using snake venom phosphodiesterase.

Figure 8:
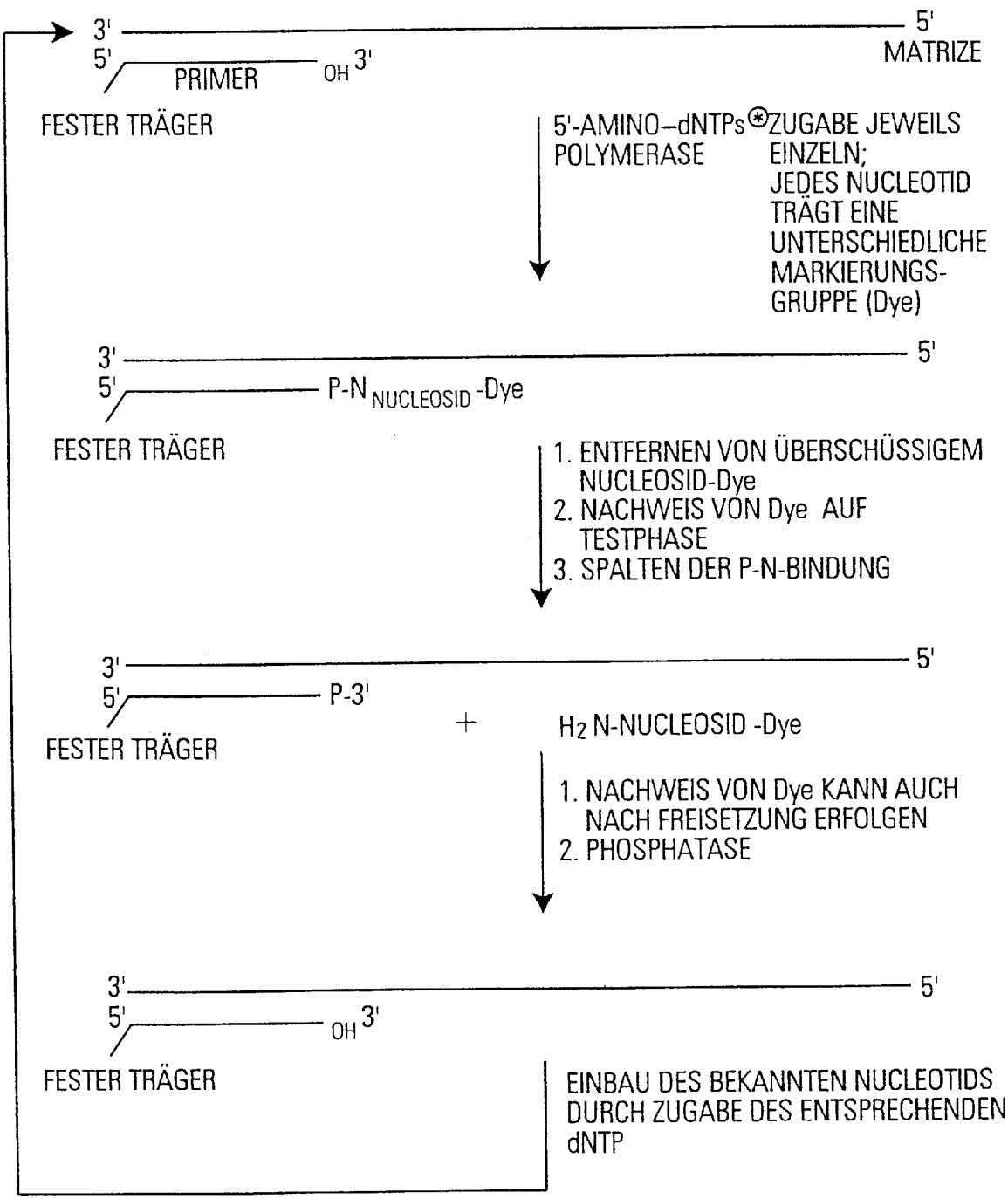
FIG. 8 shows a diagram of an electrophoresis-free, iterative sequencing method.

FIG. 8 shows an example of an electrophoresis-free and/or gel-free iterative sequencing method. This method uses dye-labelled 5'-amino-modified deoxynucleoside triphosphates, with each nucleotide carrying a different labelling group. DNA polymerase is used to add a single dye-labelled amino-modified nucleoside to the primer, with this nucleoside subsequently being eliminated once again specifically at the P—N bond. The nature of the annealed-on nucleotide can be identified from the labelling group which is detected. The polymerase can then add on the identified nucleotide in unmodified form and the previously described sequencing step can be repeated. Multiple incorporation of the same nucleotide can be detected from the intensity of the labelling, e.g. a fluorescence labelling.

Figure 9:
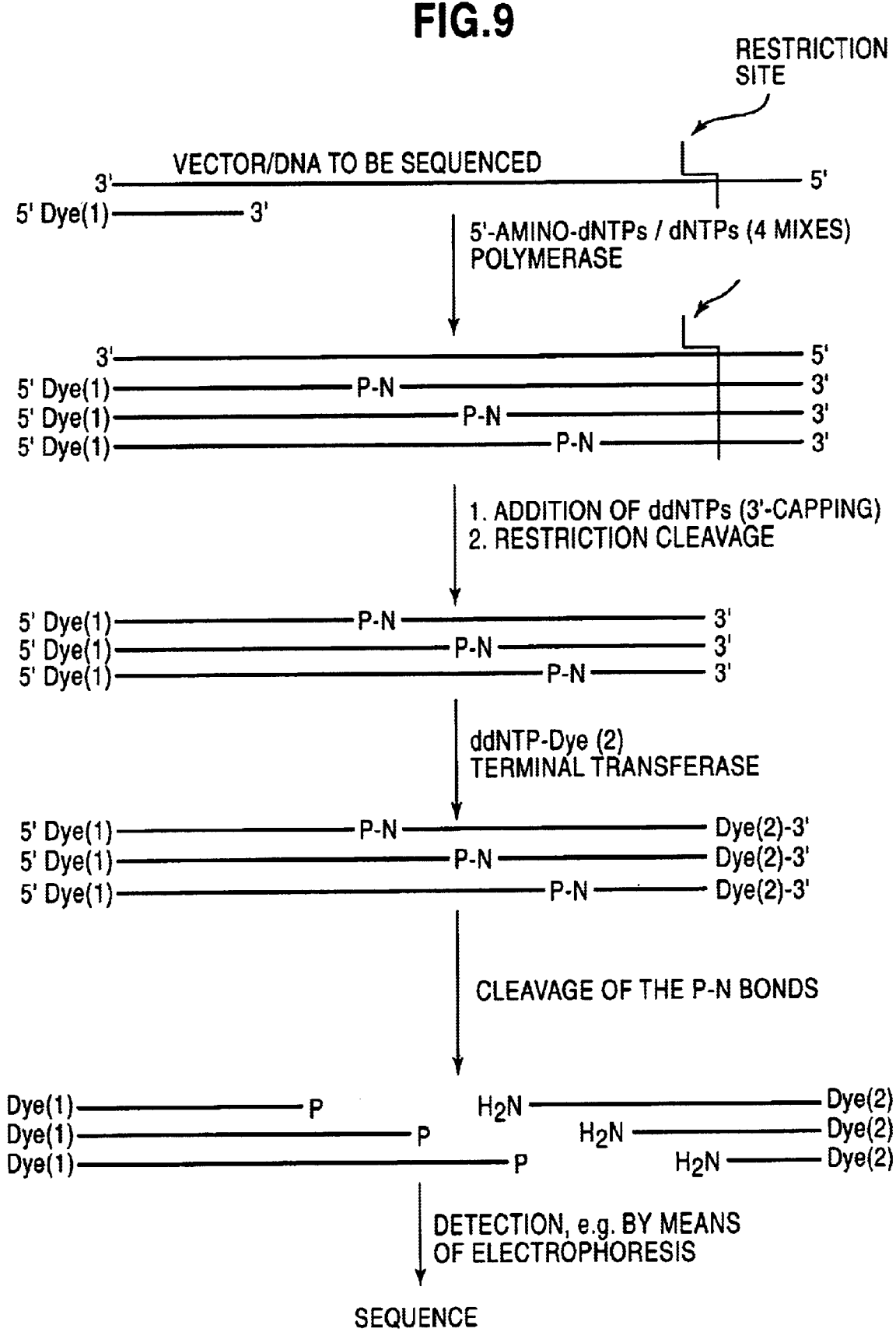
FIG. 9 shows a diagram of a bidirectional sequencing method carried out on a single nucleic acid strand.

FIG. 9 shows a bidirectional sequencing protocol within a single nucleic acid strand. For this, 5'-amino-labelled nucleosides are incorporated into nucleic acid strands as previously described. The elongation is terminated by adding chain termination molecules, e.g. ddNTPs. Defined 3' ends of the nucleic acid strands can then be generated by means of restriction cleavages. Adding a chain termination molecule, e.g. a ddNTP, which is provided with a second labelling group, and also terminal transferase results in nucleic acid strands which in each case carry two, preferably different, labelling groups at their 5' and 3' ends, respectively. Following cleavage of the P—N bonds, two sets of differently labelled DNA fragments are obtained, which fragments can be detected alongside each other in a single sequencing reaction.

Figure 10:
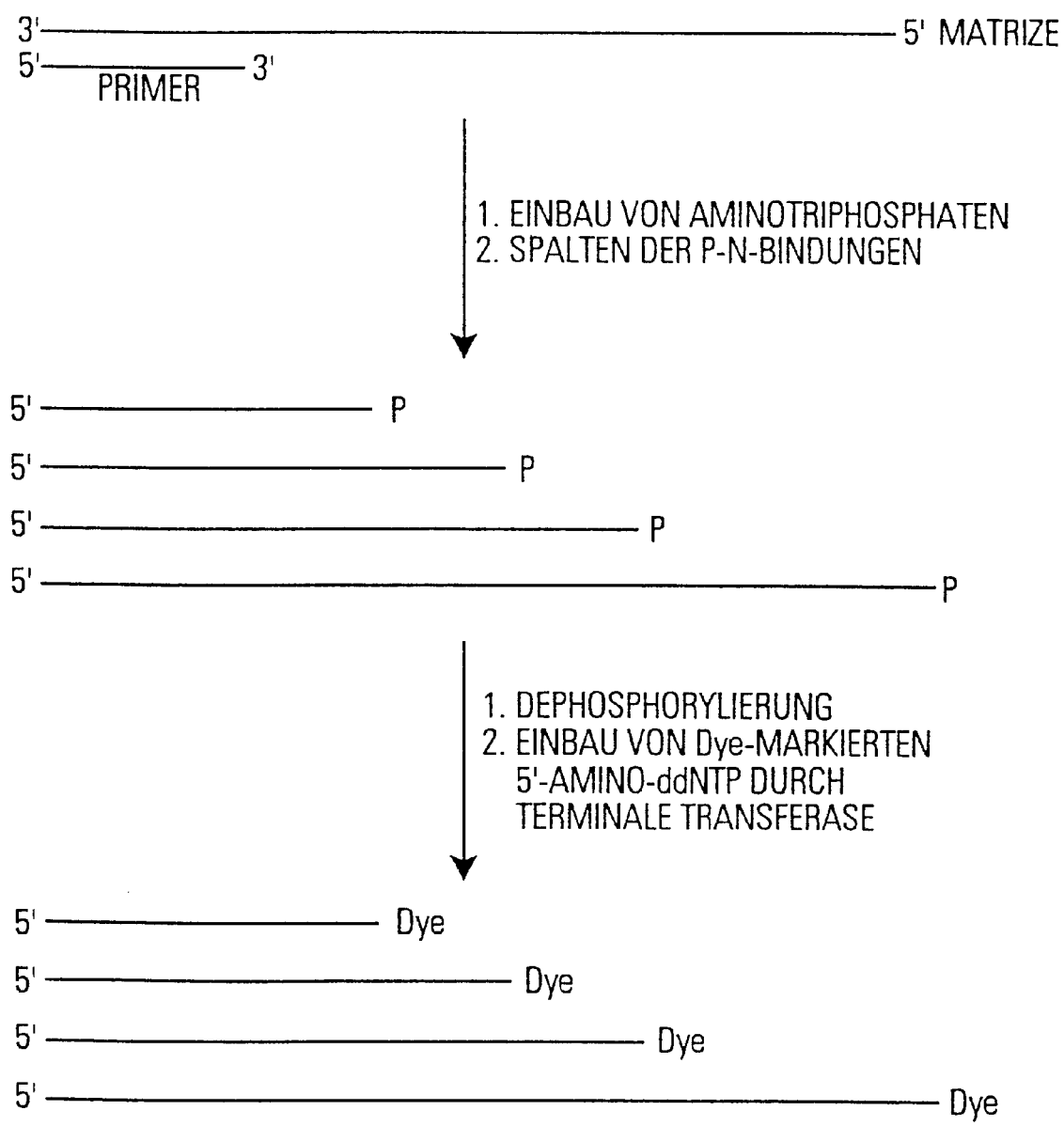
FIG. 10 shows the labelling of the nucleic acid fragments by terminal transferase after the sequencing reaction.

FIG. 10 shows a 3'-terminal introduction of labelling groups. For this, nucleic acid strands are first of all prepared by polymerization using aminotriphosphates, with these strands subsequently being cleaved at the P—N bond. The resulting nucleic acid fragments, possessing 3'-phosphate groups, are dephosphorylated and labelled by adding a labelling group-carrying chain termination molecule, e.g. a 5'-amino-ddNTP, and terminal transferase. In this way, it is possible to carry out a sequencing reaction in the absence of any type of labelling group. The labelling groups are only incorporated into the DNA fragments to be sequenced after the sequencing reaction has been concluded. In this way, problems regarding the substrate specificity of polymerases are avoided and a decrease in costs is achieved since it becomes superfluous to use labelled primer molecules.

Figure 11:
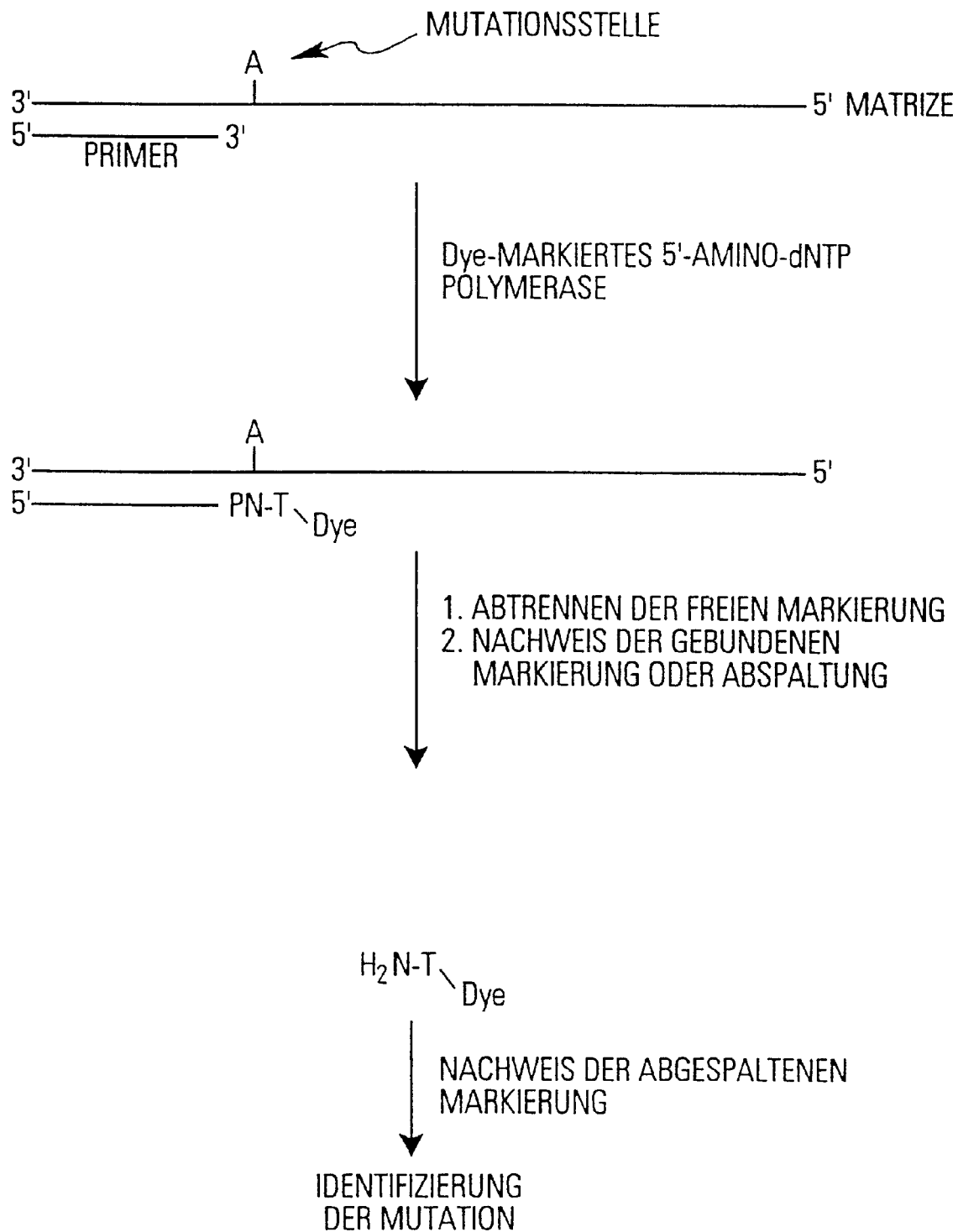
FIG. 11 shows a first embodiment for detecting point mutations.

FIG. 11 shows a first embodiment for detecting point mutations. In this case, use is made of a nucleic acid primer whose 3' end is located immediately upstream of the potential mutation site. Adding a 5'-amino-modified nucleoside triphosphate, which is provided with a labelling group, in the presence of a polymerase results in the primer being elongated by at least one nucleotide, provided the nucleotide which is complementary to the modified nucleoside triphosphate which is in each case employed is present on the template strand. The incorporation of the amino-modified, labelled nucleotide into the DNA strand, or the absence of this incorporation, can be readily detected using known methods. For this, the unincorporated nucleotide can be removed, for example by centrifuging or, in the case where binding takes place to a solid phase, by washing, and the label can then be detected in primer-bound form and/or following elimination from the primer.

Figure 12:
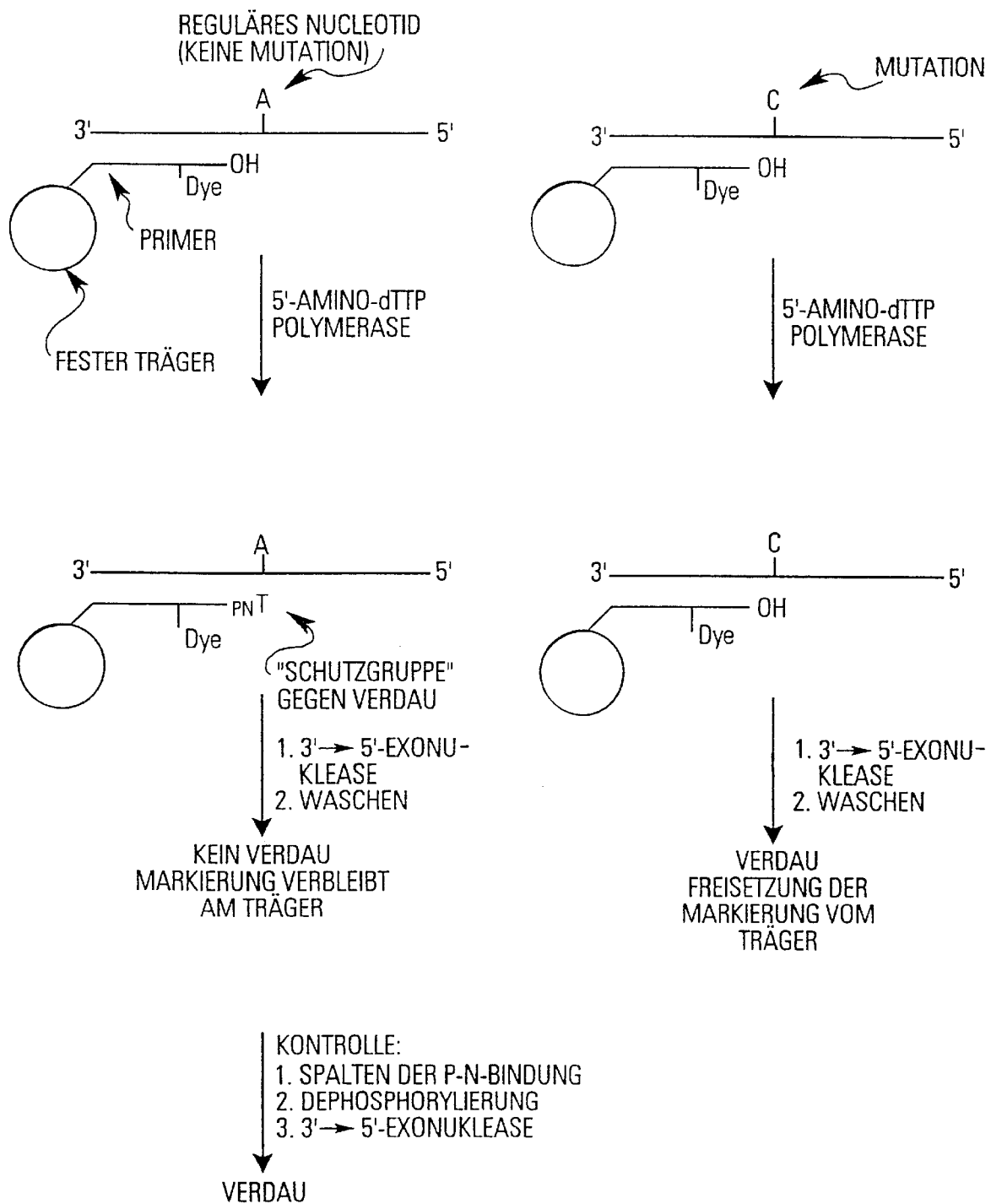
FIG. 12 shows a second embodiment for detecting point mutations.

FIG. 12 shows another embodiment for detecting point mutations. For this, use is made of a support-bound primer which carries an internal labelling group. 5'-Amino-modified nucleoside triphosphate and polymerase are then added. The primer is elongated when a particular nucleobase is present on the template strand; otherwise no 5'-aminonucleoside triphosphate is added to the primer. The reaction mixture is subsequently treated with a 3'→5'-exonuclease. After the 5'-amino-modified nucleotide has been added to the primer, no enzymic degradation by the exonuclease takes place due to the presence of the P—N bond, and the labelling group which has been incorporated in the primer remains immobilized on the solid support. If, on the other hand, no 5'-amino-modified nucleoside triphosphate is added to the primer, the latter is degraded by the exonuclease and the label is eliminated from the solid support. The retention of the label on the support, or its release, can be detected without difficulty using known methods.

Figure 13:
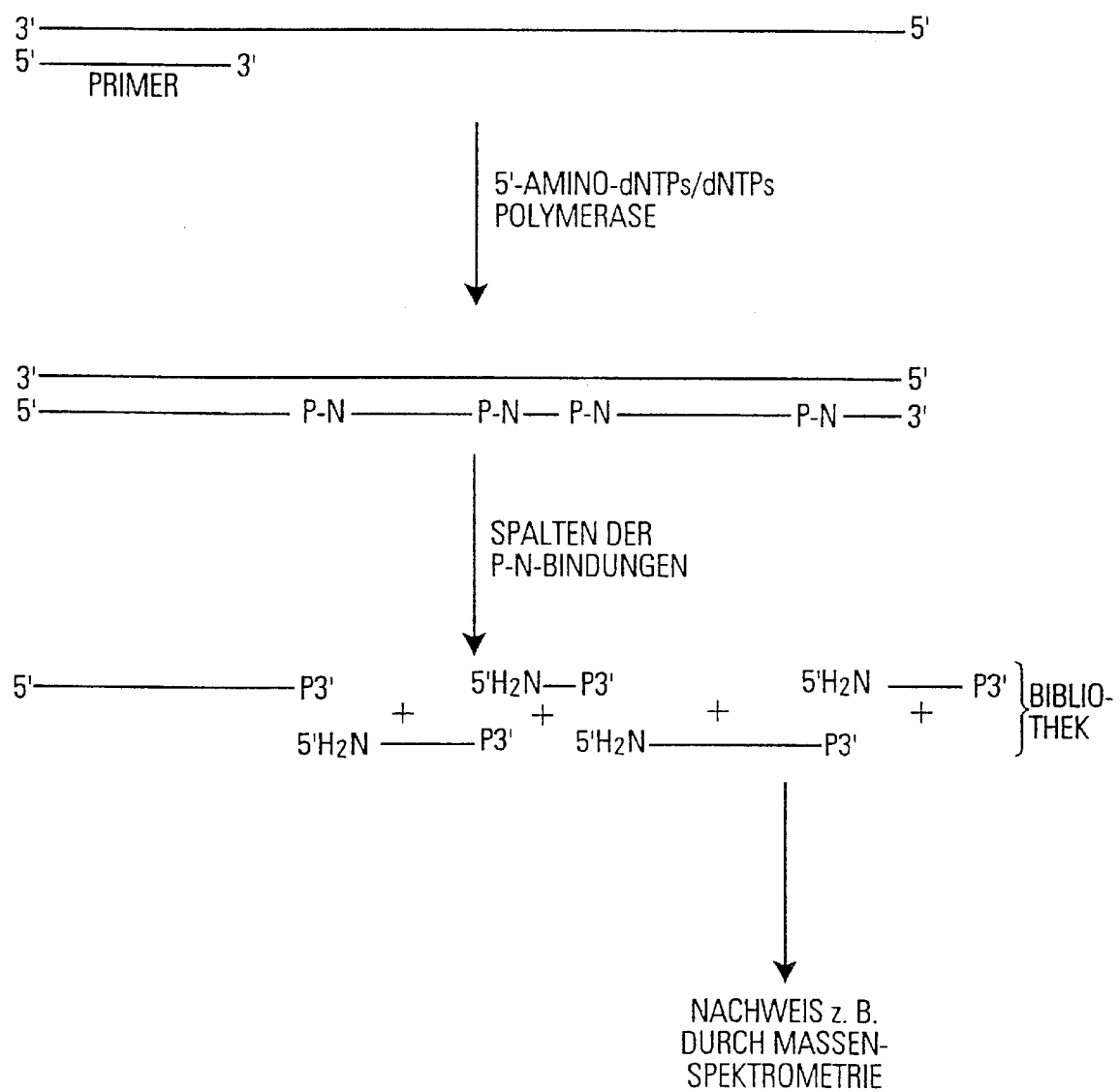
FIG. 13 shows the generation of a DNA library.

FIG. 13 shows the generation of a DNA library by the repeated incorporation of 5'-aminodeoxynucleoside triphosphate into DNA fragments. Cleaving the P—N bonds results in the generation of a large number of different DNA fragments which can either be bound to a support or, for example, be analysed by means of mass spectrometry.

EXAMPLES

1. Synthesis of Modified Nucleosides

Modified nucleosides were synthesized following Mag et al. (25). 5'-Amino-5'-deoxythymidine 5'-triphosphate and 5'-amino-2',5'-dideoxycytidine 5'-triphosphate were synthesized in accordance with Yamamoto et al. (26) by replacing the 5'-hydroxyl group with an azide group, followed by catalytic reduction to give the corresponding amine. The corresponding guanosine and adenosine derivatives were prepared by tosylating the 5'-hydroxyl group and replacing the tosyl group with lithium azide in order to avoid $N^1$—$C^5$-cyclization reactions. The purine-azide compounds were also reduced by means of catalytic hydrogenation. Following protecting group elimination, the nucleosides were triphosphorylated with trisodium trimetaphosphate in accordance with the method described by Letsinger et al. (27).

1.1 $N^4$-Benzoyl-2'-deoxycytidine 1 equivalent of 2'-deoxycytidine was dissolved in anhydrous pyridine. 5 equivalents of trimethylchlorosilane were added to this solution at room temperature. The reaction mixture was stirred for 30 min and cooled down to 0° C.; 1.2 equivalents of benzoyl chloride were then added dropwise. The mixture was first of all stirred for 30 min and then stirred for a further two hours at room temperature. The reaction was stopped by adding 10 ml of cold water at 0° C. After 20 min, the solvent was removed in vacuo. The remaining residue was dissolved in hot water and washed three times with ethyl acetate. The aqueous phase was cooled down to 4° C. and the resulting crystals were isolated by filtering and washing with cold water. The product was dried to constant weight at 50° C., over $P_2O_5$ and in vacuo.

$N^6$-Benzoyl-2'-deoxyadenosine and $N^2$-isobutyryl-2'-deoxyguanosine were prepared using the same protocol.

1.2 5'-Azido-5'-deoxythymidine 7.26 g (30 mmol) of thymidine, 9.45 g (36 mmol) of triphenylphosphine, 5.85 g (90 mmol) of sodium azide and 11.94 g (36 mmol) of tetrabromomethane were dissolved in 120 ml of dry dimethylformamide, and the mixture was stirred at room temperature for 24 h. It was then washed with 150 ml of sodium hydrogen carbonate solution, and the aqueous phase was extracted four times with 200 ml of chloroform on each occasion. The organic phase was dried with sodium sulphate and the solvent was removed in vacuo. The resulting crude product was purified by silica gel chromatography using a gradient of from 0 to 10% methanol in dichloromethane. The yield was about 76% (6.09 g).

Analysis:

TLC: $R_f$: 0.40 (chloroform:methanol=9:1; silica gel 60, $F_{254}$, Merck)

IR: $v_{as}$ ($N_3$)=2093.7 $cm^{-1}$ (s, KBr)

NMR: $\delta$-$^1$H[ppm], 270 MHz, 300 K, DMSO-$d_6$: 11.30 (s, 1H, $N^3$H); 7.47 (s, 1H, $H^6$); 6.18 (t, 1H, $H^1$); 5.39 (d, 1H, $O^3$H); 4.22 (m, 1H, $H^3$); 3.85 (m, 1H, $H^4$); 3.55 (d, 2H, $H^{5'1}$, $H^{5'2}$); 2.29 (m, 1H, $H^{2'2}$); 2.08 (m, 1H, $H^{2'1}$); 1.79 (d, 3H, $C^5$—$CH_3$)

Elemental analysis:

| Calculated | C: 44.94% | H: 4.90% | N: 26.21% |
| Found | C: 44.77% | H: 4.86% | N: 25.93% |

5'-Azido-$N^4$-benzoyl-2',5'-dideoxycytidine was prepared by the same protocol.

1.3 5'-Azido-2',5'-dideoxycytidine

5'-Azido-$N^4$-benzoyl-2',5'-dideoxycytidine was dissolved in a saturated solution of ammonia in methanol and the mixture was stirred at room temperature for 12 h. The solvent was then stripped off in vacuo and the residue was purified chromatographically using dichloromethane containing a gradient of from 0 to 15% methanol as the eluent.

1.4 5'-O-(4-Methylbenzenesulphone)-$N^6$-benzoyl-2'-deoxyadenosine and 5'-O-(4-methylbenzenesulphone)-$N^2$-isobutyryl-2'-deoxyguanosine In each case 1 equivalent of $N^6$-benzoyl-2'-deoxyadenosine and $N^2$-isobutyryl-2'-deoxyguanosine was dissolved in dry pyridine. 3 equivalents of 4-methylbenzenesulphonyl chloride were then added to this solution at room temperature. The reaction mixture was stirred for 45 min and then cooled on ice and quenched with 5 ml of water. After 15 min, the solution was concentrated by evaporation and the oily residue was taken up in ethyl acetate. The solution was washed twice with 5% $NaHCO_3$, water and saturated salt solution, dried over sodium sulphate and concentrated by evaporation in vacuo. The residue was purified chromatographically using a gradient of from 0 to 10% methanol in dichloromethane as the eluent.

1.5 5'-Azido-2',5'-dideoxyadenosine and 5'-azido-2',5'-dideoxyguanosine

In each case 1 equivalent of the compounds prepared in Example 1.4 was taken up in dry N,N-dimethylformamide, after which five equivalents of lithium azide were added. The solution was stirred at 50° C. for 5 h. A five-fold volume of dichloromethane was then added and the mixture was washed three times with water. The organic phase was dried with sodium sulphate and filtered off, and the solvent was stripped off. The protecting groups were eliminated, and the crude products were purified, as described in connection with the preparation of 5'-azido-2',5'-dideoxycytidine.

1.6 5'-Amino-5'-deoxythymidine 150 ml of absolute methanol were degassed by being frozen and thawed five times in vacuo. 1.5 g (5.62 mmol) of 5'-azido-5'-deoxythymidine were dissolved in this methanol, and a small quantity of platinum dioxide hydrate catalyst was added. Hydrogen gas was passed into the solution and the mixture was stirred at room temperature for 2 h. The solvent was removed following filtration through Celite. No further purification was required. The yield was virtually quantitative.

Analysis:

TLC: $R_f$: 0.05 (dichloromethane:methanol=9:1; silica gel 60 $F_{254}$, Merck)

IR: $v_{as}$ ($N_3$)=not present (KBr)

NMR: $\delta$-$^1$H [ppm], 270 MHz, 300 K, DMSO-$d_6$: 7.63 (s, 1H, $H^6$); 6.15 (t, 1H, $H^1$); 5.15 (d, 1H, $O^3$H); 4.21 (m, 1H, $H^3$); 3.65 (m, 1H, $H^4$); 2.73 (d, 2H, $H^{5'1}$, $H^{5'2}$); 1.95–2.15 (m, 2H, $H^{2'1}$, $H^{2'2}$); 1.79 (d, 3H, $C^5$—$CH_3$)

Mass spectrometry: ESI (+)

Calculated: 242.2 Da Found: 242.1 Da

5'-Amino-2',5'dideoxycytidine, 5'-amino-2',5'-dideoxyadenosine and 5'-amino-2',5'-dideoxyguanosine were prepared by the same protocol.

1.7 5'-Amino-5'-deoxythymidine 5'-triphosphate 2 mg (1 equivalent) of 5'-amino-5'-deoxythymidine and 13.4 mg (5 equivalents) of trisodium trimetaphosphate were dissolved in 100 µl of sterile water (pH 8.50), after which this solution was stirred at room temperature for 30 h and then stored at −80° C. For the sequencing experiments, an aliquot was removed directly from the reaction mixture without any further purification.

5'-Amino-2',5'-dideoxycytidine 5'-triphosphate, 5'-amino-2',5'-dideoxyadenosine 5'-triphosphate and 5'-amino-2',5'-dideoxyguanosine 5'-triphosphate were prepared by the same synthesis protocol.

Analysis:

Mass spectrometry: ESI(−):

5'-Amino-2',5'-dideoxyadenosine 5'-triphosphate:

Calculated: 490.199 Da Found: 488.8 Da (M−H); 510.9 Da (M−2H+Na); 532.7 Da (M−2H+2Na)

5'-Amino-2',5'-dideoxycytidine 5-triphosphate:

Calculated: 466.173 Da Found: 464.8 Da (M−H); 486.8 Da (M−2H+Na)

5'-Amino-2',5'-dideoxyguanosine 5'-triphosphate:

Calculated: 506.198 Da Found: 504.8 Da (M−H); 526.8 Da (M−2H+Na) 548.7 Da (M−3H+2Na)

5'-Amino-5'-deoxythymidine 5'-triphosphate:

Calculated: 481.184 Da Found: 479.9 Da (M−H); 480.6 Da (M); 501.8 Da (M−2H+Na) 523.8 Da (M−3H+2Na)

2. Sequencing Reaction

The implementation of the sequencing reaction is described using the T lane as an example. The sequencing reaction for the A, C and G lanes can be carried out in an analogous manner.

0.3 µl of primer, e.g. universal or reverse primer (fluoroscein isothiocyanate-labelled; 2 µM), 0.3 µl of DMSO, 1.2 µl of ss-M13 MP18 (+) DNA and 0.6 µl of annealing buffer (1 M Tris-HCl, pH 7.6; 100 mM MgCl$_2$) were added together per mix. The solution was incubated at 70° C. for 3 min and cooled down to room temperature over a period of 20 min.

0.60 µl of a DNTP mixture (in each case 250 µM DATP, dCTP and dGTP and 50 µM dTTP), 0.44 µl of 5'-amino-dTTP (from the reaction mixture of Example 1.7) and 0.25 µl of T7 polymerase (8 U/µl) were added to this solution and the whole was incubated at 37° C. for 10 min.

5'-Amino-dATP, 5'-amino-dCTP and 5'-amino-dGTP were used for the A, C and G lanes, respectively.

4 µl of stop solution (95% deionized formamide, 20 mM EDTA, 0.05% xylene cyanole; 0.05% bromophenol blue) are subsequently added.

The P—N bonds were cleaved in order to prepare a sequenceable mixture of nucleic acid fragments. The following alternative methods are available for doing this:

1. Cleaving by raising the temperature:
    heating for 40 minutes at 95° C. (heating for 20 minutes is also possible)
2. Cleaving under acid conditions:
    adding from 2 to 5 µl of 1 N HCl, incubating for five minutes at room temperature, neutralizing with 2 to 5 µl of 1 N NaOH, and denaturing for five minutes at 95° C.
3. Cleaving with microwaves:
    treating the sample with microwave radiation for 30 min at 900 W.

As an alternative to this, it is also possible to employ enzymic cleavage methods using exonucleases or endonucleases, in particular using 3'→5' exonucleases such as 3'→5' snake venom phosphodiesterase. For this, 10 mU (3.2 µl) of 3'→5' snake venom phosphodiesterase are added, after which the mixture is incubated at 40° C. for 10 min and denaturation is carried out at 95° C. for 5 min.

The fragment mixture was subsequently analysed, for example by polyacrylamide gel electrophoresis. For this, 5 µl of the reaction mix were loaded onto the gel. Alternatively, the reaction mix can be stored at −20° C. and then denatured at 95° C. for 3 min before being applied to the gel.

REFERENCES:

(1) Sanger, F., Nicklen, S., Coulson, A.R., *Proc. Natl. Acad. Sci. USA* 74, 5463–5467, 1977

(2) Pieles, U., Zurcher, W., Schär, M., Moser, H. E., *Nucl. Acids. Res.* 21, 3191–3196, 1993

(3) a) Jones, D. H., *BioTechniques* 22, 938–946, 1997 b) Brenner, S., WO 95/27080, 1995

(4) Ronaghi, M., Kharamouhamed, S., Pettersson, B., Uhlén, M., Nyrn, P., *Anal. Biochem.* 242, 84–89, 1996

(5) Maxam, A. M., Gilbert, W., *Proc. Natl. Acad. Sci. USA* 74, 560–564, 1977

(6) a) Gish, G., Eckstein, F., *Science* 240, 1520–1522, 1988 b) Nakayame, K. L., Gish, G., Eckstein, F., Vosberg, H.-P., *Nucl. Acids Res.* 16, 9947–9959, 1988 c) Labeit, S., Lehrrach, H., Goody, R. S., *DNA* 5, 173–177, 1986 d) Porter, K. W., Briley, J. D., Ramsay Shaw, B., *Nucl. Acids Res.* 25, 1611–1617, 1997

(7) a) Barnes, W. M., *J. Mol. Biol.* 119, 83–99, 1978 b) Hamilton, R. T., Wu, R., *J. Biol. Chem.* 249, 2466–2472, 1974

(8) a) Canard, B., Sarfati, R. S., *Gene* 148, 1–6, 1994 b) Canard, B., Sarfati, S., PCT Int. Appl. WO 94 23064; PCT/FR94/00345, 1994

(9) a) Dramane, R., Labat, I., Bruckner, I., Crkvenjakov, R., *Genomics* 4, 114–128, 1989 b) Dramane, R., Dramane, S., Stroszka, Z., Paunesku, T., Labat, I., Zeremski, M., Snoddy, J., Funkhouser, W. K., Koop, B., Hood, L., Crkvenjakov, R., *Science* 260, 1649–1652, 1953 c) Bains, W., Smith, G. C., *J. Theor. Biol.* 135, 303–307, 1988

(10) a) Baldwin, M. A., *Natural Products reports*, 33–44, 1995: b) Wolter, M. A., Engels, J. W., *Eur. Mass Spectrom.* 1, 583–590, 1995 c) Nordhoff, E., Karas, M., Cramer, R., Hahner, S., Hillenkamp, F., Kirpekar, F., Lezius, A., Muth, J., Meier, C., Engels, J. W., *J. Mass Spectrom*, 30, 99–112, 1995; d) Little, D. P., Chorush, R. A., Speir, J. P., Senko, M. W., Kelleher, N. L., McLafferty, F. W., *J. Am. Chem. Soc.* 116, 4893–4897, 1994; e) Grotjahn, L., Frank, R., Bl öcker, H., *Nucl. Acids Res.* 10, 4671–4678, 1983

(11) Löber, G., Kittler, L., *PhiuZ* 27, 113–117, 1996

(12) a) Ansorge, W., Sprout, B., Stegemann, J., Schwager, C., *J. Biochem. Biophys. Meth.* 13, 315–323, 1986; b) Smith, L. M., Sanders, J. Z., Kaiser, R. J., Hughes, P., Dodd, C., Conell, C. R., Heiner, C., Kent, S. B. H., Hood, L. E., *Nature* 321, 674–679, 1986

(13) Voss, H., Schwager, C., Wirkner, U., Zimmermann, J., Erfle, H., Hewitt, N. A., Rupp, T., Stegemann, J., Ansorge, W., *Meth. Mol. Cell. Biol.* 3, 30–34, 1992

(14) Lee, L. G., Connell, C. R., Woo, S. L., Cheng, R. D., McArdle, B. F., Fuller, C. W., Halloran, N. D., Wilson, R., *Nucl. Acids Res.* 20, 2471–2483, 1992

(15) Murray, V., *Nucl. Acids Res.* 17, 8889, 1989

(16) Rosenthal, A., Coutelle, O., Craxton, M., *Nucl. Acids Res.* 21, 173–174, 1993

(17) Amersham Life Science product catalogue 1996, 89

(18) Kilger, C., Pääbo, S., *Biol. Chem.* 378, 99–105, 1997

(19) Smith, L. M., Fung, S., Hunkapillar, T. J., Hood, L. E., *Nucl. Acids Res.* 13, 2399–2412, 1985

(20) Current protocols in Molecular Biology. Vol 1, Section 3.10, John Wiley and Sons, Series Editor: Virginia Benzon Chanda

(21) Bruick, R. K., Koppitz, M., Joyce, G. F., Orgel, L. E., *Nucl. Acids Res.* 25, 1309–1310, 1997
(22) Biomagnetic Techniques in Molecular Biology, Technical Handbook, second edition, Dynal, Oslo, Norway, 156–157
(23) Landegren, U., Laboratory protocols for mutation detection, Oxford University Press, 1996, ISBN 0-19-857795-8
(24) Nikiforov, T. T., Rendle, R., B., Goelet, B., Rogers, Y-H., Kotewicz, M., L., Anderson, S., Trainor, G., L., Knapp, M. R., Genetic Bit Analysis: a solid phase method for typing single nucelotide polymorphisms, *Nucl. Acids Res.* 22, 4167–4175, 1994
(24a) Alexandrova, L. A., Skoblov, A., Y., Jasko, M. V., Victorova, L. S., Krayevsky, A. A., *Nucl. Acids Res.* 26, 778–786, 1998
(25) Mag. M., Engels, J. W., *Nucl. Acids Res.* 17, 5973–5988, 1989
(26) Yamamoto, I., Sekine, M., Hata, T., *J. Chem. Soc. Perkin Trans. I* 1, 306–310, 1980
(27) Letsinger, R. L., Wilkes, J. S., Dumas, L. B., *J. Am. Chem. Soc.*, 292–293, 1972

What is claimed is:

1. A process for detecting nucleic acids in a sample, the process comprising
    a) synthesizing by a nucleic acid amplification reaction multiple copies of a double-stranded nucleic acid from a single-stranded nucleic acid in the sample by the enzymatic incorporation in the single-stranded nucleic acid of a compound of formula (I)

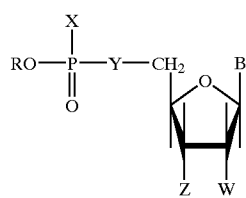

(I)

wherein:
B is a nucleobase,
W and Z is each independently, $OR^1$, $SR^1$, $N(R^1)_2$ or $R^1$, wherein $R^1$ is hydrogen or a lipophilic radical,
X is $OR^2$, $SR^2$ or $B(R^2)_3$, wherein $R^2$ is hydrogen, a cation or a lipophilic radical,
Y is $NR^3$ or S, wherein $R^3$ represents hydrogen or a lipophilic radical, and
R is hydrogen, a cation or a lipophilic radical,
    b) subjecting the double-stranded nucleic acid comprising at least one nucleobase of a compound of formula I to site-directed cleavage to obtain nucleic acid fragments comprising a 5' modified end by the site-directed cleavage reaction, and
    c) detecting the nucleic acid fragments of step b).

2. The process according to claim 1, wherein the enzyme is selected from the group consisting of DNA-dependent DNA polymerases, DNA-dependent RNA polymerases, and RNA-dependent DNA polymerases.

3. The process according to claim 1, wherein site-directed cleavage is mediated by:
    (i) an increase in temperature,
    (ii) an acid,
    (iii) microwave,
    (iv) laser and/or
    (v) enzymatic digestion.

4. The process according to claim 1, wherein the nucleic acid amplification reaction comprises a polymerase chain reaction.

5. The process according to claim 1, wherein the compound of formula I is incorporated into a nucleic acid bound to a solid support.

6. The process according to claim 1, wherein one or more labeling groups are incorporated into the nucleic acid fragments obtained by site-directed cleavage.

7. The process according to claim 6, wherein the labeling groups are added at the 5' end and/or 3' end of the nucleic acid fragments.

8. The process according to claim 1, wherein the nucleic acid fragments obtained by site-directed cleavage are immobilized on a solid support.

9. The process according to claim 8, wherein the support comprises a surface comprising at least one of metal, glass, ceramic or plastic.

10. The process according to claim 8, wherein the support is selected from the group consisting of microparticles and biochips.

11. The process according to claim 1, wherein the site-directed cleavage generates a library of modified nucleic acid fragments.

12. The process according to claim 1, wherein the detecting step comprises mass spectrometric analysis.

13. The process according to claim 1, wherein the detecting step comprise electrophoresis.

14. The process according to claim 1, wherein the detecting step comprises a sequence determination.

15. The process according to claim 14, characterized in that the sequence determination comprises a cycle sequencing and a nucleic acid amplification.

16. The process according to claim 14, wherein the sequence determination is bi-directional for a single strand of the nucleic acid fragment.

17. A process for identifying a mutation in a nucleic acid comprising the steps of
    a) providing a primer wherein the 3' end is immediately upstream of the mutation,
    b) adding the primer to the process according to claim 1, and
    c) detecting the mutation by incorporation of a compound of formula I of claim 1.

18. A process for preparing nucleic acid fragments which comprises the steps of:
    (a) synthesizing by a nucleic acid amplification reaction multiple copies of a double-stranded nucleic acid from a single-stranded nucleic acid in the sample by the enzymatic incorporation in the single-stranded nucleic acid of a compound of formula (I)

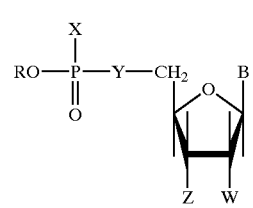

(I)

wherein:
B is a nucleobase,
W and Z is each independently, $OR^1$, $SR^1$, $N(R^1)_2$ or $R^1$, wherein $R^1$ is hydrogen or a lipophilic radical,
X is $OR^2$, $SR^2$ or $B(R^2)_3$, wherein $R^2$ is hydrogen, a cation or a lipophilic radical, Y is $NR^3$ or S, wherein $R^3$ represents hydrogen or a lipophilic radical, and R is hydrogen, a cation or a lipophilic radical, and (b) subjecting the double-stranded nucleic acid comprising at least one nucleobase of a compound of formula I to site-directed cleavage to obtain nucleic acid fragments comprising a 5' modified end by the site-directed cleavage reaction.

19. The process according to claim 18, wherein the 5' end of the nucleic acid fragments comprises an HY—CH2— group, wherein Y is defined in claim 1.

20. The process according to claim 18, wherein the nucleic acid fragments comprise a phosphate group at the 3' end.

21. Reagent kit for detecting nucleic acids, comprising at least one compound of formula (I) as defined in claim 1, components for a nucleic acid amplification reaction, an enzyme capable of incorporating the at least one compound into a single stranded nucleic acid, and detection components.

* * * * *